United States Patent
Shin et al.

(10) Patent No.: US 11,567,048 B2
(45) Date of Patent: Jan. 31, 2023

(54) JIG FOR PRESSING GAS ANALYSIS MONOCELL, AND GAS ANALYSIS DEVICE INCLUDING SAME

(71) Applicant: LG CHEM, LTD., Seoul (KR)

(72) Inventors: Ju Kyung Shin, Daejeon (KR); Joon Sung Bae, Daejeon (KR); Gyu Ok Hwang, Daejeon (KR); In Young Cha, Daejeon (KR)

(73) Assignee: LG Energy Solution, Ltd., Seoul (KR)

( * ) Notice: Subject to any disclaimer, the term of this patent is extended or adjusted under 35 U.S.C. 154(b) by 644 days.

(21) Appl. No.: 16/608,222

(22) PCT Filed: Nov. 14, 2018

(86) PCT No.: PCT/KR2018/013902
§ 371 (c)(1),
(2) Date: Oct. 25, 2019

(87) PCT Pub. No.: WO2019/098673
PCT Pub. Date: May 23, 2019

(65) Prior Publication Data
US 2020/0049678 A1    Feb. 13, 2020

(30) Foreign Application Priority Data

Nov. 17, 2017 (KR) .................. 10-2017-0154185
Nov. 14, 2018 (KR) .................. 10-2018-0139729

(51) Int. Cl.
*G01N 33/00* (2006.01)
*H01M 10/42* (2006.01)

(52) U.S. Cl.
CPC ..... *G01N 33/0009* (2013.01); *G01N 33/0062* (2013.01); *H01M 10/4285* (2013.01)

(58) Field of Classification Search
CPC .. H01M 10/4285; H01M 10/48; H01M 50/30; G01N 33/0009; G01N 33/0062
See application file for complete search history.

(56) References Cited

U.S. PATENT DOCUMENTS 6,558,438 B1 * 5/2003 Satoh ................ H01M 10/0413
429/94
10,640,638 B2 * 5/2020 An ............................ C08J 5/18
(Continued)

FOREIGN PATENT DOCUMENTS

CN          105229818 A     1/2016
EP            3300162 A1    3/2018
(Continued)

OTHER PUBLICATIONS

International Search Report issued in corresponding International Patent Application No. PCT/KR2018/013902, dated Mar. 6, 2019.
(Continued)

*Primary Examiner* — Peter J Macchiarolo
*Assistant Examiner* — Mohammed E Keramet-Amircolai
(74) *Attorney, Agent, or Firm* — Morgan, Lewis & Bockius LLP

(57) ABSTRACT

A jig for pressing a gas analysis monocell according to the present invention comprises: a first plate and a second plate which face each other with a monocell therebetween; a first auxiliary pad positioned between the first plate and the monocell; and a second auxiliary pad positioned between the second plate and the monocell, wherein the first plate and the second plate are formed of a thermosetting resin. When analyzing a gas generated from the monocell during a primary charge, the jig for pressing the monocell according to the present invention presses the thin monocell to prevent (Continued)

a gap from forming between electrodes due to the primary charge, and thus has an effect of deriving more reliable analysis results.

15 Claims, 8 Drawing Sheets

(56) References Cited

U.S. PATENT DOCUMENTS

| | | | | |
|---|---|---|---|---|
| 11,061,263 | B2* | 7/2021 | Fujita | G02F 1/13439 |
| 2005/0080183 | A1* | 4/2005 | Chung | B32B 15/092 |
| | | | | 428/458 |
| 2006/0117832 | A1* | 6/2006 | Nakashima | G01N 33/0009 |
| | | | | 73/23.2 |
| 2011/0223462 | A1* | 9/2011 | Kim | H01M 50/20 |
| | | | | 429/120 |
| 2014/0193685 | A1* | 7/2014 | Lim | H01M 10/658 |
| | | | | 429/99 |
| 2014/0234677 | A1* | 8/2014 | Yoon | H01M 50/20 |
| | | | | 429/89 |
| 2015/0064547 | A1* | 3/2015 | Ahn | H01M 10/0413 |
| | | | | 429/162 |
| 2015/0090048 | A1* | 4/2015 | Kim | G01R 1/0408 |
| | | | | 73/856 |
| 2017/0155256 | A1* | 6/2017 | Fujimaki | H01M 10/4235 |
| 2019/0229322 | A1* | 7/2019 | Do | H01M 50/60 |
| 2019/0288355 | A1* | 9/2019 | An | H01M 10/0525 |
| 2019/0288357 | A1* | 9/2019 | Son | B60L 50/64 |
| 2019/0382574 | A1* | 12/2019 | An | C08L 33/062 |
| 2020/0049678 | A1* | 2/2020 | Shin | H01M 10/486 |
| 2020/0127269 | A1* | 4/2020 | Park | H01M 50/548 |
| 2020/0350638 | A1* | 11/2020 | Hwang | G05D 16/2013 |
| 2021/0218107 | A1* | 7/2021 | Hwang | H01M 10/52 |

FOREIGN PATENT DOCUMENTS

| | | |
|---|---|---|
| JP | 2001-035523 A | 2/2001 |
| JP | 2001-297798 A | 10/2001 |
| JP | 2002-313437 A | 10/2002 |
| JP | 2011-070911 A | 4/2011 |
| JP | 2011-181812 A | 9/2011 |
| JP | 2013-105662 A | 5/2013 |
| JP | 2013-149378 A | 8/2013 |
| KR | 10-2001-0070357 A | 7/2001 |
| KR | 10-2009-0071034 A | 7/2009 |
| KR | 10-2013-0044776 A | 5/2013 |
| KR | 2013-0123762 A | 11/2013 |
| KR | 20130128033 A | 11/2013 |
| KR | 10-2016-0024104 A | 3/2016 |
| KR | 20160072571 A | 6/2016 |
| KR | 10-2016-0081394 A | 7/2016 |
| KR | 2017-0031940 A | 3/2017 |
| KR | 10-1730961 B1 | 4/2017 |
| WO | 2017047937 A1 | 3/2017 |

OTHER PUBLICATIONS

Extended European Search Report dated May 29, 2020 issued by the European Patent Office in a corresponding European patent application No. 18878575.2.

* cited by examiner

[Fig. 1]
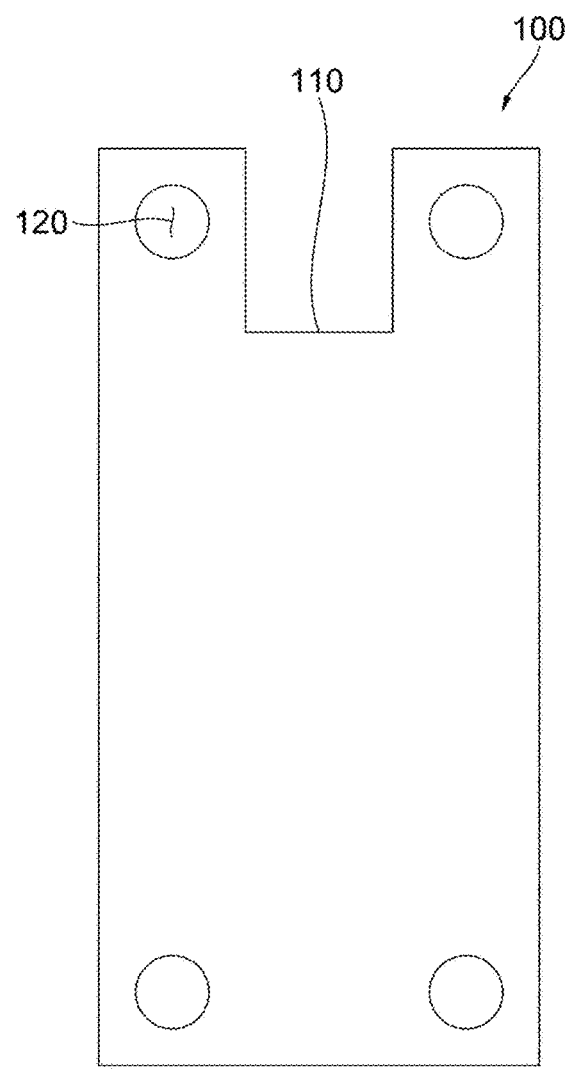

[Fig. 2]
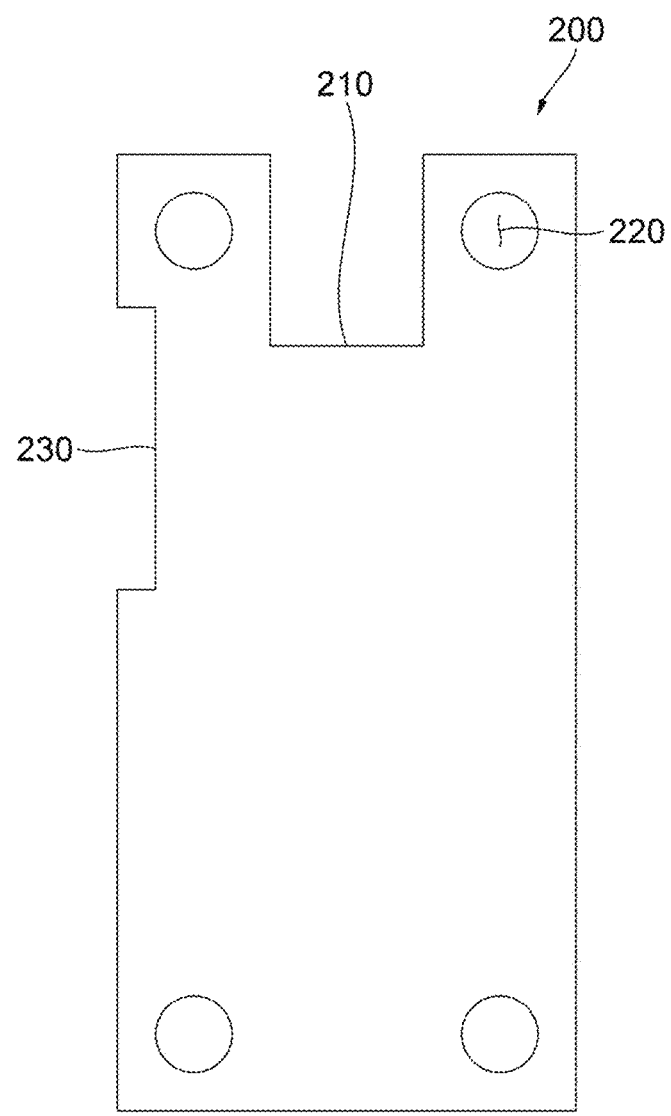

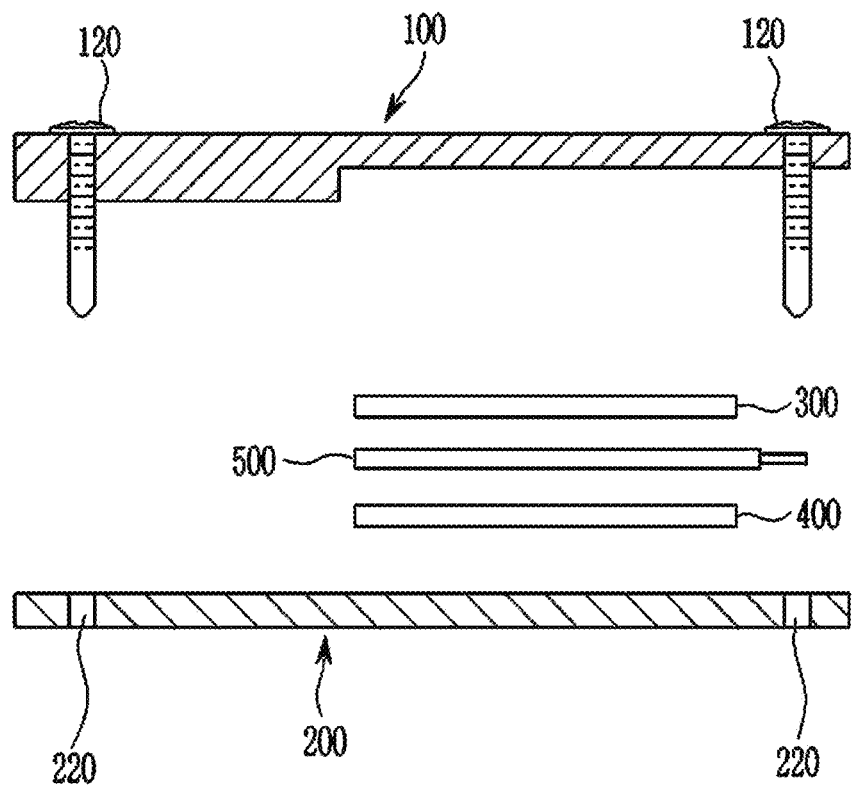
[Fig. 3]

[Fig. 4]
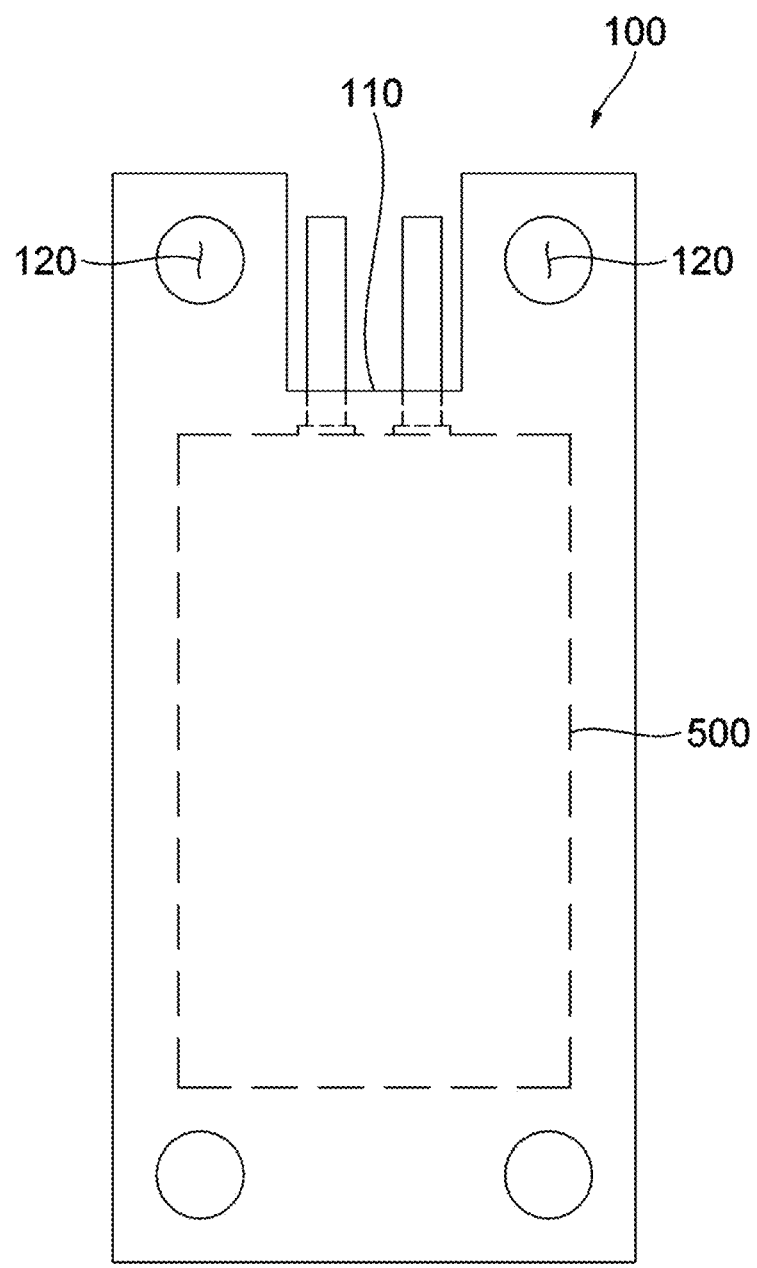

[Fig. 5]
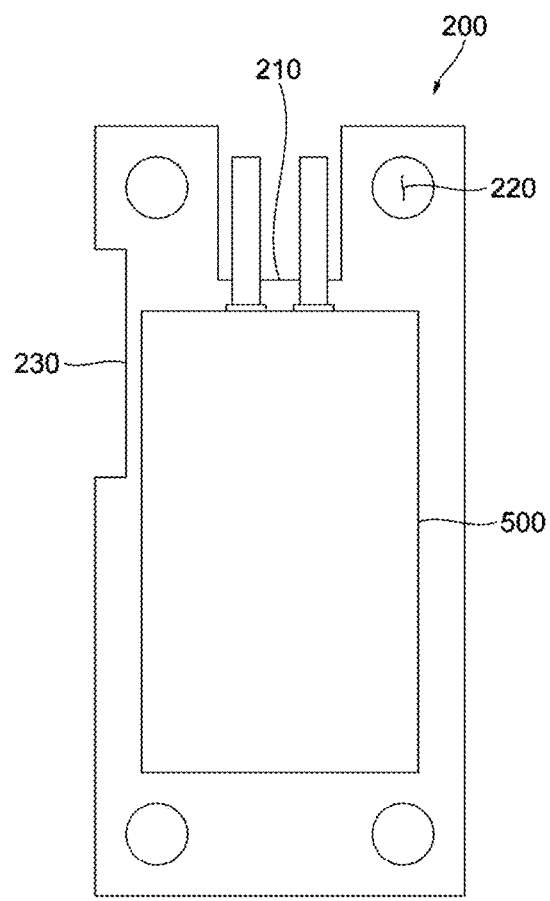

[Fig. 6]
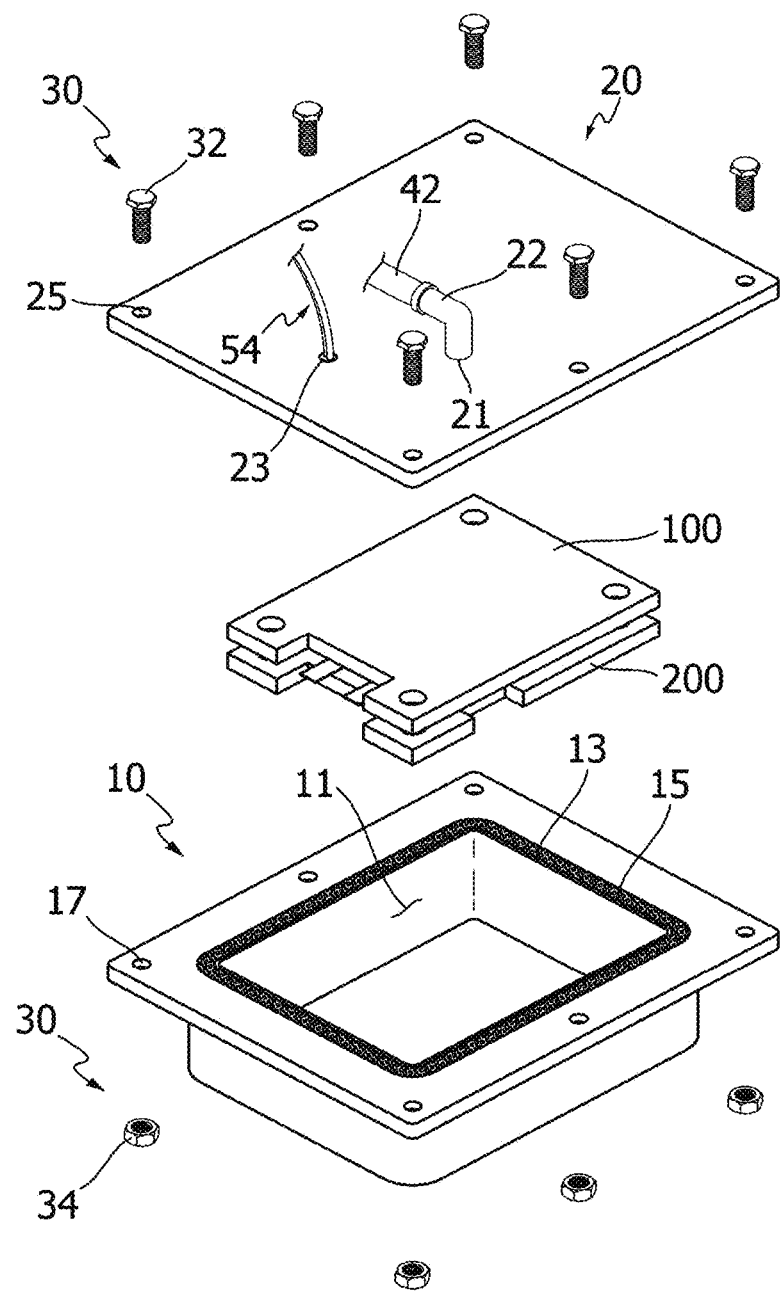

[Fig. 7]
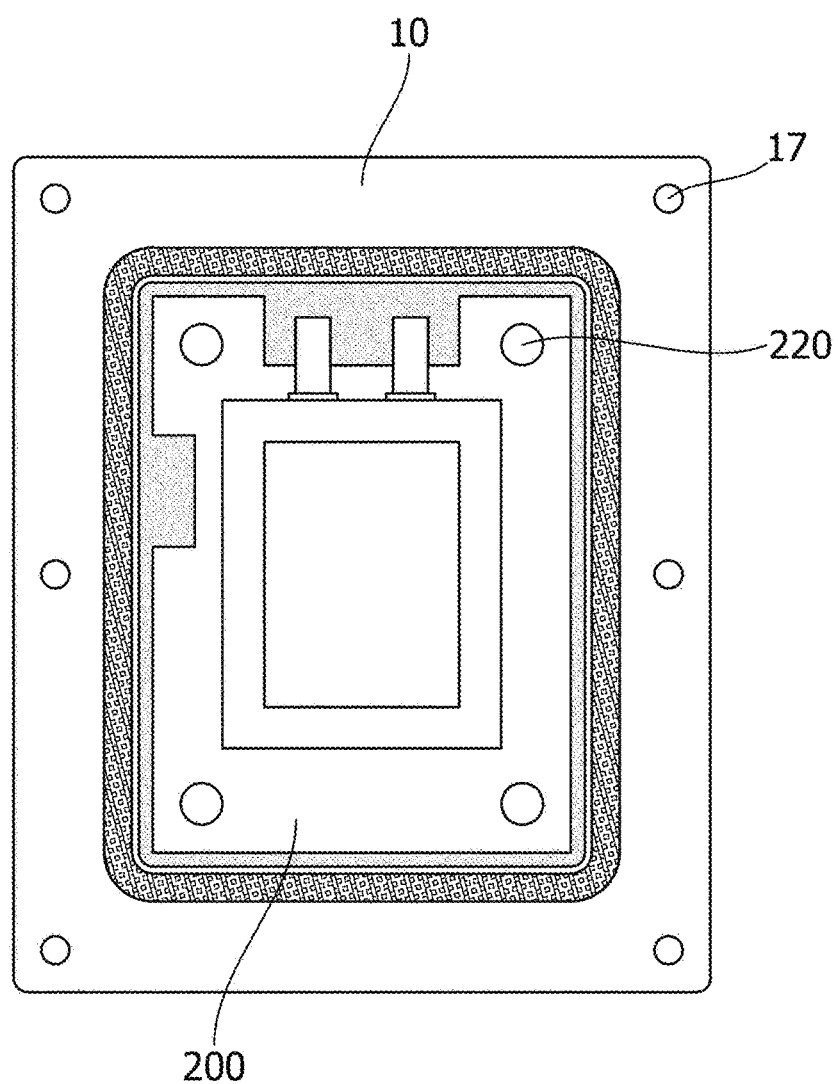

[Fig. 8]
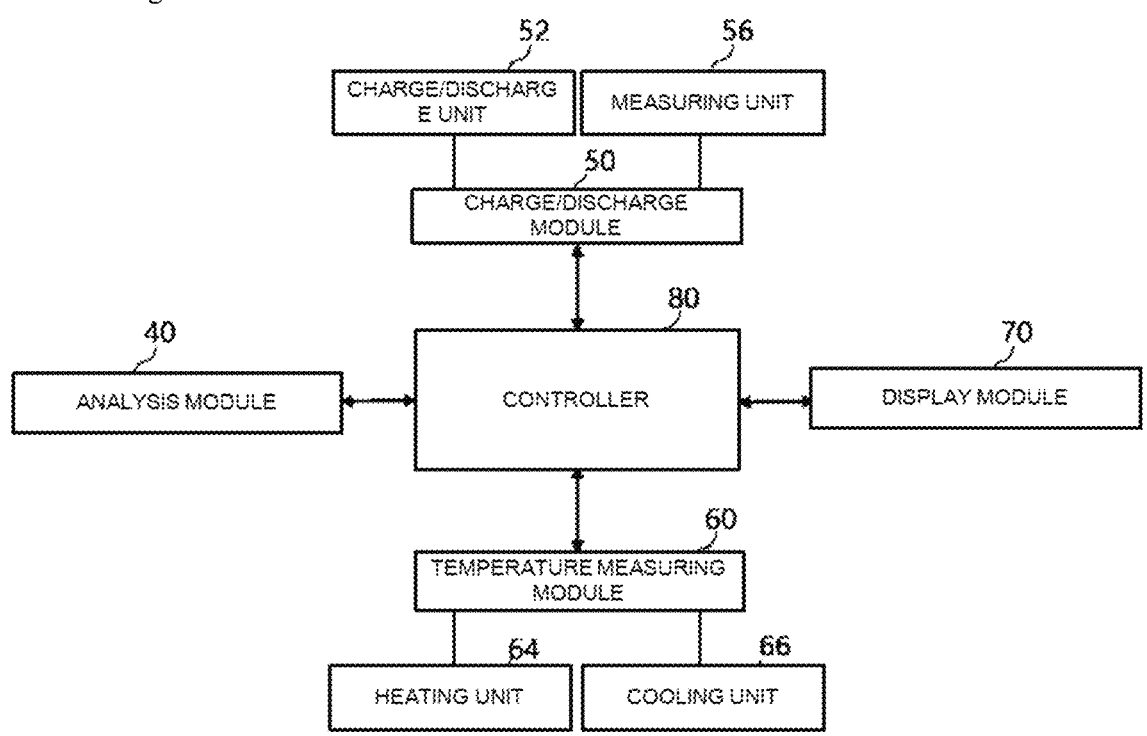

JIG FOR PRESSING GAS ANALYSIS MONOCELL, AND GAS ANALYSIS DEVICE INCLUDING SAME

TECHNICAL FIELD

This application claims the benefit of priority based on Korean Patent Application No. 10-2017-0154185 filed on Nov. 17, 2017 and Korean Patent Application No. 10-2018-0139729 filed on Nov. 14, 2018, and the content of these Korean Patent Applications are incorporated herein as part of the present specification.

The present invention relates to a pressurizing jig of a monocell, and more particularly, to a pressurizing jig capable of preventing a lifted phenomenon between electrodes by pressurizing a monocell at the time of analyzing gases of the monocell, and a gas analysis device including the same.

BACKGROUND ART

Secondary batteries have electrical properties such as ease of application and high energy density. Such secondary batteries are generally used in electric vehicles (EVs) or hybrid vehicles (HVs), which are driven by electric driving sources as well as portable devices.

In general, a secondary battery is charged or discharged by an electrochemical reaction of an active material, a metal plate, and an electrolyte, and gas may be generated by the electrochemical reaction inside the secondary battery while the charging or discharging operation is performed.

These gases are by-products of the secondary battery's electrochemical reactions, and need to be accurately and precisely analyzed for improvement of the performance of the secondary battery, optimization of the structure of the secondary battery, the enhancement of the charge/discharge efficiency through the adjustment of elements such as active materials and electrolytes, and minimization of ancillaries.

Since small battery cells are relatively small in size, it is relatively easy to extract gases and analyze components of the gases, but since medium-large cells are large is size and capacity, it is difficult to carry out quantitative and qualitative analysis of internal gases. Thus, as an alternative, a monocell is produced and gas analysis is performed under conditions that simulate it as a medium-large cell. However, since the monocell is very thin, the electrolyte is excessively injected. As such, a lifted phenomenon occurs between the electrodes, and thus it should be pressurized.

The conventional gas analysis device does not have a device configuration capable of pressurizing the monocell, and thus, it is necessary to develop a gas analysis device capable of pressurizing the monocell.

DISCLOSURE

Technical Problem

It is an object of the present invention to provide a pressurizing jig capable of pressurizing a monocell and a gas analysis device including the same in a gas analysis device for analyzing the amount and composition of gases generated during initial charging of a monocell in real time.

Technical Solution

A pressurizing jig of a monocell for gas analysis according to an embodiment of the present invention includes a first plate and a second plate which face each other having the monocell therebetween, a first auxiliary pad positioned between the first plate and the monocell, and a second auxiliary pad positioned between the second plate and the monocell, in which the first plate and the second plate contain a thermosetting resin.

In an embodiment of the present invention, the first plate may be quadrangular and may include at least one coupling member positioned in at least one corner.

In an embodiment of the present invention, the second plate may be quadrangular and may include at least one coupling hole positioned in at least one corner.

In an embodiment of the present invention, the coupling member may correspond to the coupling hole.

In an embodiment of the present invention, the second plate may include a gas passage part through which internal gases of the monocell are movable.

In an embodiment of the present invention, the first plate may include a first groove in which an electrode lead of the monocell is positioned.

In an embodiment of the present invention, the second plate may include a second groove in which an electrode lead of the monocell is positioned.

In an embodiment of the present invention, the thermosetting resin may be Bakelite.

In an embodiment of the present invention, the first auxiliary pad and the second auxiliary pad may be made of silicon rubber.

In an embodiment of the present invention, a thickness of each of the first plate and the second plate may be between 1 and 20 mm.

In an embodiment of the present invention, a thickness of each of the first auxiliary pad and the second auxiliary pad may be between 1 to 10 mm.

A gas analysis device of a monocell according to an embodiment of the present invention may include a lower chamber which has a shape corresponding to that of the pressurizing jig and includes a receiving groove into which the pressurizing jig is detachably fitted, and an upper chamber including a gas hole formed to discharge internal gases generated in the monocell, a collecting tube connected to the gas hole to guide the internal gases discharged through the gas hole to an outside, and a charge/discharge hole through which a connecting member for electrically connecting a charge/discharge unit to the monocell penetrates.

In an embodiment of the present invention, the gas analysis device may further include an analysis module for analyzing the internal gases flown in from the chamber, a charge/discharge module for charging/discharging the monocell, a temperature measuring module for measuring a temperature of the monocell, a display module for displaying an analysis result for the internal gases of the monocell, and a controller for controlling operation of the modules.

In an embodiment of the present invention, the temperature measuring module may include a temperature sensing member for measuring the temperature of the monocell, a heating unit for raising the temperature of the monocell, and a cooling unit for lowering the temperature of the monocell.

In an embodiment of the present invention, the charge/discharge hole may be sealed in a manner that a sealing material is applied in a state that the connecting member is penetrated.

Advantageous Effects

According to a monocell pressurizing jig of the present invention, when analyzing gases generated in a monocell during primary charging, the monocell having a small thickness is pressurized to thereby prevent a lifted phenomenon between electrodes by the primary charging by pressurizing a thin cell, thereby providing more reliable analysis results.

In addition, since the gas analysis device of the present invention can perform gas analysis using a monocell that simulates a medium-large cell, the amount of generation, components, composition, gas generation time according to temperatures, and gas generation time according to voltages of internal gases of the medium-large cell may be easily analyzed in real time.

BRIEF DESCRIPTION OF THE DRAWINGS

FIGS. 1 and 2 are diagrams schematically showing an example of a plane of a pressurizing jig of a monocell for gas analysis according to an embodiment of the present invention.

FIG. 3 is a diagram schematically showing an example in which a monocell is disposed on a pressurizing jig of a monocell for gas analysis according to an embodiment of the present invention.

FIGS. 4 and 5 are diagrams schematically showing an example of a structure in which a monocell is mounted on a pressing jig of a monocell for gas analysis according to an embodiment of the present invention.

FIG. 6 is an exploded perspective view of a gas analysis device of a monocell according to an embodiment of the present invention.

FIG. 7 is a schematic diagram showing a structure in which a pressurizing jig of the present invention is coupled to a gas analysis device of the present invention.

FIG. 8 is a block diagram for explaining a control system of a gas analysis device of the present invention.

DETAILED DESCRIPTION OF THE PREFERRED EMBODIMENTS

Hereinafter, embodiments of the present invention will be described in detail with reference to the accompanying drawings. The present invention may, however, be embodied in many different forms and should not be construed as limited to the embodiments set forth herein.

In order to clearly illustrate the present invention, parts not related to the description are omitted, and the same or similar components are denoted by the same reference numerals throughout the specification.

In addition, since the sizes and thicknesses of the respective components shown in the drawings are arbitrarily shown for convenience of explanation, the present invention is not necessarily limited to those shown in the drawings. In the drawings, the thicknesses are enlarged to clearly indicate layers and regions. In the drawings, for the convenience of explanation, the thicknesses of some layers and regions are exaggerated.

Also, when a portion such as a layer, a film, an area, a plate, etc. is referred to as being "on" another portion, this includes not only the case where the portion is "directly on" the another portion but also the case where further another portion is interposed therebetween. Conversely, when a part is "directly over" another part, it means that there is no other part in the middle. Also, to be "on" a reference portion means to be located above or below the reference portion and does not necessarily mean to be "on" toward the opposite direction of gravity.

Also, throughout the specification, when an element is referred to as "including" an element, it is understood that the element may include other elements as well unless specifically stated otherwise.

In addition, throughout the specification, when referred to as "plan view", it means when the target portion is viewed from above, and when referred to as "cross-sectional view", it means when a vertically-cut cross-section of the target portion is viewed from the side.

A pressurizing jig of a monocell for gas analysis according to an embodiment of the present invention will be described with reference to FIGS. 1 to 3.

FIGS. 1 and 2 are diagrams schematically showing an example of a plane of a pressing jig of a monocell for gas analysis according to an embodiment of the present invention. FIG. 3 is a diagram schematically showing an example in which a monocell is disposed on a pressing jig of a monocell for gas analysis according to an embodiment of the present invention.

Referring to FIGS. 1 to 3, a pressurizing jig of a monocell for gas analysis according to the present embodiment includes a first plate 100, a second plate 200, a first auxiliary pad 300, and a second auxiliary pad 400.

The first plate 100 is generally rectangular in shape, and a first groove 110 is positioned above the plane. In addition, the first plate 100 includes fastening members 120 positioned at corners. The fastening members 120 may be located at four corners of the rectangular first plate 100, respectively. Each of the fastening members 120 may be a screw or a clip.

The second plate 200 is generally rectangular in shape, and a second groove 210 is positioned above the plane. In addition, the second plate 200 includes fastening holes 220 positioned at corners. The fastening holes 220 may be located at four corners of the rectangular second plate 200, respectively. In addition, the second plate 200 includes a gas passage part 230 through which the gas generated in the monocell moves.

A monocell 500 may be located between the first plate 100 and the second plate 200. Here, the monocell 500 is a monocell for simulating a medium-large secondary battery cell. The medium-large secondary battery cell should be interpreted to mean a medium-large cell or a medium-large cell module including at least one cell having a capacity of 20 Ah or more.

During the initial charging of a secondary battery, a solid electrolyte interphase (SEI) film is formed, which requires analysis of a gas generated therein. Analysis of the amount and composition of gases generated during the initial charging of the secondary battery is the main data for determining the end point of the initial charging.

However, in the case of medium and large cells, the size and capacity are large, which makes it difficult to analyze the amount and composition of gases generated during initial charging. Accordingly, the amount and composition of the gases generated during the initial charging of the monocell may be analyzed using the monocell 500 that simulates the medium and large secondary battery cells. As such, when the monocell is used, the analysis is relatively quick and easy compared to the gas analysis of vehicles to which medium-large secondary battery cells are applied.

The pressurizing jig of the monocell for gas analysis according to the present embodiment may be used for real-time analysis of the amount and composition of gases generated during initial charging of the monocell.

The first auxiliary pad 300 is positioned between the first plate 100 and the monocell 500. The second auxiliary pad 400 is positioned between the second plate 200 and the monocell 500. The first auxiliary pad 300 and the second auxiliary pad 400 may have a quadrangular shape.

The fastening members 120 positioned in the first plate 100 correspond to the fastening holes 220 located in the second plate 200, respectively. When analyzing the components of gases generated in the monocell 500, each fastening member 120 may be fastened to each fastening hole 220.

The monocell 500, which is a monocell that simulates a medium-large cell, has a small thickness, and an excessive amount of electrolyte is injected into the monocell 500. Therefore, when the initial charge and discharge are performed, pressurization at a predetermined pressure or more is required due to a lifted phenomenon between electrodes.

As illustrated in FIG. 3, the fastening members 120 positioned in the first plate 100 correspond to the fastening holes 220 located in the second plate 200, respectively. Each fastening member 120 may be fastened to each fastening hole 220. The fastening hole 220 located in the second plate 200 provides an installation space for the fastening member 120 located in the first plate 100. The fastening holes 220 are formed at four corners of the second plate, and a thread that can be screwed with the fastening member 120 is formed on an inner circumferential surface of the fastening hole 220. In this case, the electrode lead of the monocell 500 is located in the first groove 110 of the first plate 100 and the second groove 210 of the second plate 200. The electrode lead of the monocell 500 may be connected to a charge/discharge module described below to charge or discharge the monocell 500.

In the present embodiment, as the fastening member 120 positioned on the first plate 100 is fastened to the fastening hole 220 positioned on the second plate 200, the monocell 500 positioned between the first plate 100 and the second plate 200 may be pressurized with a predetermined pressure or more. That is, the fastening member 120 positioned on the first plate 100 may be fastened to the fastening hole 220 positioned on the second plate 200, to thereby pressurize the monocell 500 with the first plate and the second plate 200.

At this time, since the first plate 100 and the second plate 200 should pressurize the monocell in order to prevent the lifted phenomenon between the electrodes, a material that does not bend under certain strength is preferable. In addition, since the analysis of the amount and composition of the gases generated during the initial charging of the monocell 500 should be performed even at a high temperature, a material having strong heat resistance is preferable. Therefore, the first plate 100 and the second plate 200 may be made of a thermosetting resin.

The thermosetting resin first flows upon application of heat, but then hardens with a three-dimensional branch structure. It does not melt quickly when reheated. The molding material of the thermosetting resin has a relatively low molecular weight and exhibits fluidity by heating, but becomes a three-dimensional structure of a seam according to an added curing agent, a catalyst, and a crosslinking reaction, and polymerizes to prevent the natural movement of molecules not to be melt. For this reason, it does not soften even after reheated. Thermosetting resins have high hardness and are excellent in mechanical properties and electrical insulation properties, and there are various types and characteristics of each. Examples of such a thermosetting resin include a phenol resin, a melamine resin, and a silicone resin.

Among the said thermosetting resins, Bakelite which is a phenol resin is the most preferably used to form the first plate and the second plate of this invention. The Bakelite is an organic polymer synthesized using benzene and formaldehyde, and its chemical name is polyoxybenzylmethylenglycolanhydride. Bakelite has a sufficient rigidity that does not deform with pressure, and has good heat resistance and does not soften even when heated to 150 to 180° C. As such, the Bakelite is not deformed even by high temperature gas, and thus it is most preferable as a raw material of the first plate and the second plate of the present invention.

Each thickness of the first plate and the second plate may be 1 to 20 mm, preferably 3 to 15 mm, most preferably 5 to 12 mm. If the thickness of each of the first plate and the second plate is less than 1 mm, the monocell cannot be pressurized with sufficient pressure, and if the thickness of the first plate and the second plate is greater than 20 mm, it may be difficult for them to be mounted at the inside of the gas analysis device, which is not preferable.

The first auxiliary pad 300 and the second auxiliary pad 400 are positioned between the first plate 100 and the monocell 500 and between the second plate 200 and the monocell 500, respectively, to thereby relieve the shock at the time of pressurization and prevent damage to a surface of the monocell 500.

The first auxiliary pad 300 and the second auxiliary pad 400 should have elasticity and an insulating property in consideration of their usage, and should not be deformed even at high temperatures because they are used in a jig for gas analysis. Silicone rubber is preferred as a material satisfying such characteristics. Silicone rubber is a polymer in which organic carbons are bonded with silicon atoms. It is most preferable as an auxiliary pad material of the present invention because it has almost no change in physical properties even in extreme environments from minus 100 to 300 degrees Celsius, and has heat resistance, fire resistance, and high pressure insulation.

Each thickness of the first auxiliary pad and the second auxiliary pad may be 1 to 10 mm, preferably 2 to 8 mm, more preferably 3 to 7 mm. If the thickness of the auxiliary pad is less than 1 mm, it is not preferable because there is almost no buffering effect, and if the thickness of the auxiliary pad exceeds 10 mm, there is a problem that it is not suitable to apply an appropriate pressure to the monocell.

Meanwhile, in the present exemplary embodiment, the first plate 100, the second plate 200, the first auxiliary pad 300, and the second auxiliary pad 400 have a rectangular shape, but are not limited thereto.

A structure, in which the monocell 500 is mounted on the pressurizing jig of the monocell for gas analysis according to the exemplary embodiment of the present invention, will be described with reference to FIGS. 4 and 5.

FIGS. 4 and 5 are diagrams schematically showing an example of a structure in which a monocell is mounted on a pressing jig of a monocell for gas analysis according to an embodiment of the present invention.

Referring to FIGS. 4 and 5, the monocell 500 is positioned between the first plate 100 and the second plate 200. A first auxiliary pad (not shown) is located between the first plate 100 and the monocell 500, and a second auxiliary pad (not shown) is located between the second plate 200 and the monocell 500. Here, the monocell 500 may be a monocell that simulates a secondary battery cell of medium and large capacity.

In this case, the electrode lead of the monocell 500 is located in the first groove 110 of the first plate 100 and the second groove 210 of the second plate 200. The electrode lead of the monocell 500 may be connected to a charge/discharge module described below to charge or discharge the monocell 500.

The second plate 200 includes a gas passage part 230. The gas passage part 230 allows gases to pass by so that the amount and composition of the gases generated during the initial charging of the monocell 500 can be analyzed.

When the monocell 500 is charged and discharged by applying a voltage or a current to the electrode lead of the monocell 500 from an external power source, a lifted phenomenon occurs between the electrodes of the monocell 500, and in order to prevent such a lifted phenomenon, the monocell 500 is pressed by the first plate 100 and the second plate 200 by fastening the fastening member 120 and the fastening hole 220.

The gases pass through the gas passage part 230 in order to analyze the amount and composition of the gases generated during the initial charging of the monocell 500.

The pressurized jig of the monocell is mounted inside the gas analysis device of the secondary battery cell to pressurize the monocell, thereby preventing the lifting of the initial charging of the monocell, thereby enabling a more reliable analysis.

Hereinafter, the gas analysis device of the monocell on which the pressuring jig of the monocell is mounted will be described in detail.

FIG. 6 is an exploded perspective view of a gas analysis device of a monocell according to an embodiment of the present invention.

Referring to FIG. 6, the gas analysis device of the monocell according to the preferred embodiment of the present invention has a shape corresponding to that of the pressurizing jig of the present invention, and includes: a lower chamber 10 having a receiving groove into which the pressurizing jig is detachably fitted; and an upper chamber 20 including a gas hole 21 formed to discharge the internal gases generated in the monocell 500, a collecting tube 22 connected to the gas hole to guide the internal gases discharged through the gas hole to the outside, and a charge/discharge hole 23 through which the connecting member 54 for electrically connecting the charge/discharge unit to the secondary battery cell penetrates.

FIG. 7 is a plan view of a lower chamber 10 showing a state in which the monocell pressurizing jig of the present invention has been mounted. The lower chamber 10 is a member for receiving a pressurizing jig equipped with the monocell 500 to be analyzed. The lower chamber is preferably formed of a metal material, but is not limited thereto.

As shown in FIGS. 6 and 7, the lower chamber 10, which has a shape corresponding to the pressurizing jig of the monocell, includes a receiving groove 11 in which the pressurizing jig of the monocell is detachably fitted, a sealing groove 13 formed along the circumference of the receiving groove 11, a sealing member 15 for sealing a space between the receiving groove 11, provided in the sealing groove 13, and the upper chamber 20, and a lower coupling hole 17 which is formed in the edge portion and at which the coupling bolt 32 is coupled with a screw.

The receiving groove 11 provides a receiving space of the monocell pressurizing jig. The receiving groove 11 has a shape corresponding to the monocell pressurizing jig so that the monocell pressurizing jig can be detachably fitted as shown in FIGS. 6 and 7.

The lower coupling hole 17 provides an installation space of the coupling bolt 32 with the coupling member 30 to be described later. The lower coupling hole 17 is formed in plural at predetermined intervals at the edge of the lower chamber 10 provided along the circumference of the sealing groove 13. A screw thread that can be screwed with the coupling bolt 32 is formed on the inner circumferential surface of the lower coupling hole 17.

The sealing groove 13 provides an installation space of the sealing member 15 to be described later. The sealing groove 13 is formed along the circumference of the receiving groove 11 so as to face the bottom surface of the upper chamber 20 when the upper chamber 30 and the lower chamber 10 are coupled as shown in FIG. 6.

The sealing member 15 is a member for sealing a space between the upper chamber 20 and the receiving groove 11. The sealing member 15 is installed in the sealing groove 13 so as to surround the receiving groove 11, as shown in FIG. 6. The installation method of a sealing member is not specifically limited.

The sealing member 15 has been described as being installed in the sealing groove 13, but is not limited thereto. That is, the sealing member 15 may be installed on the bottom of the upper chamber 20 so as to seal a space between the bottom of the upper chamber 20 and the receiving groove 11.

The lower coupling hole 17 provides an installation space of the coupling bolt 32 with the coupling member 30 to be described later. The lower coupling hole 17 is formed in plural at predetermined intervals at the edge of the lower chamber 10 provided along the circumference of the sealing groove 13. A screw thread that can be screwed with the coupling bolt 32 is formed on the inner circumferential surface of the lower coupling hole 17.

The upper chamber 20 is a member for closing the opening of the receiving groove 11 in which the monocell pressurising jig has been accommodated. The upper chamber 20 is coupled to the upper portion of the lower chamber 10 to close the opening of the receiving groove 11, as shown in FIG. 6.

As illustrated in FIG. 6, the upper chamber 20 includes a gas hole 21 formed to discharge the internal gases generated in the monocell 500, a collecting tube 22 for guiding the internal gases discharged to the outside through the gas hole 21, a charge/discharge hole 23 for installing the connecting member 54 of a charge/discharge module 50 to be described later, and a upper coupling hole 25 to which a coupling bolt 32 of a coupling member 30 to be described later is screwed.

The gas hole 21 provides a discharge port for discharging the internal gases generated in the monocell 500 from the receiving groove 11. As shown in FIG. 6, the gas hole 21 is formed by penetrating the upper chamber 20 so as to be linked to the receiving groove 11. Therefore, the internal gases of the monocell generated inside the monocell and discharged into the receiving groove 11 may be discharged through the gas hole 21.

The collecting tube 22 is a member for collecting the internal gases discharged through the gas hole 21 of the upper chamber 20. As shown in FIG. 6, one end of the collecting tube 22 is coupled to the upper surface of the upper chamber 20 to thereby be connected to the gas hole 21, and the other end of the collecting tube 22 is coupled to one end of the gas tube 42 of the analysis module 40 to be described later. Here, the other end of the collecting tube 22 may be screwed to one end of the gas tube 42 by the nut 22a. As such, as the collecting tube 22 is provided, the internal gases discharged through the gas hole 21 may be collected by the collecting tube 22 and guided to the gas tube 42 of the analysis module 40.

The charge/discharge hole 23 provides a passage for installing the connecting member 54 of the charge/discharge module 50 to be described later. As illustrated in FIG. 6, the charge/discharge hole 23 is formed by penetrating the upper chamber 20 so that the connecting member 54 may pass therethrough. In addition, in order to prevent the internal gases from leaking through the charge/discharge hole 23, the charge/discharge hole 23 is coated with a sealing material (not shown) in a state that the connecting member 54 is penetrated. As the sealing material (not shown), silicone rubber is preferably used, but is not limited thereto.

In an embodiment of the present invention, a temperature sensing hole (not shown) is further formed in the upper chamber 20. The temperature sensing hole provides a passage for installing the temperature sensing member of the temperature measuring module. The temperature sensing hole is formed through the upper chamber so that the conductive wires of the temperature sensing member can pass therethrough. In addition, in order to prevent the internal gases from leaking through the temperature sensing hole, the temperature sensing hole may be coated with a sealing material while the conductive wires are penetrated. The sealing material may be silicone rubber, but is not limited thereto.

Further, it has been described that the temperature sensing hole is formed separately from the charge/discharge hole 23, but is not limited thereto. That is, the temperature sensing hole and the charge/discharge hole may be integrally formed.

The upper coupling hole 25 provides an installation space of the coupling bolt 32 of the coupling member 30 to be described later. A plurality of upper coupling holes 25 are formed at predetermined intervals at edge portions of the upper chamber 20 so as to correspond to the lower coupling holes 17, respectively. A screw thread that can be screwed with the coupling bolt 32 is formed on the inner circumferential surface of the upper coupling hole 25.

Next, the coupling member 30 is a member for tightly coupling the lower chamber 10 with the upper chamber 20 so that the receiving groove 11 is closed. As shown in FIG. 6, the coupling member 30 includes a plurality of coupling bolts 32 screwed with the lower coupling hole 17 and the upper coupling hole 25, and a nut 34 which is screwed with the coupling bolt 32 to allow the lower chamber 10 to be in close contact with the upper chamber 20

The head of the coupling bolt 32 is supported on the upper surface of the upper chamber 20, and the end portion of the coupling bolt 32 is screwed to the upper coupling hole 25 and the lower coupling hole 17 corresponding thereto. Correspondingly, the nut 34 is screwed into the end portion of the coupling bolt 32 passing through the lower coupling hole 17. Then, the upper chamber 20 and the lower chamber 10 are tightened by the bolt head and the nut 34 to be tightly coupled. Therefore, since the sealing member 15 is pressed against the bottom of the upper chamber 20 more strongly by the coupling member 30, the sealing member 15 can more reliably seal a space between the bottom of the upper chamber 20 and the receiving groove 11.

FIG. 7 shows a form in which the pressurizing jig of the present invention is accommodated in the gas analysis device of the present invention according to one embodiment of the present invention. Referring to FIG. 7, a second plate 200 having a second auxiliary pad (not shown) attached thereon has been inserted into the receiving groove 11 in a manner that is detachable from the lower chamber. After the monocell 500, which is the subject of analysis, is mounted on a second auxiliary pad (not shown) attached to the second plate 200 for gas analysis, the first auxiliary pad of the first plate is positioned to contact the monocell 500. Thereafter, the first plate and the second plate are coupled in a manner that the coupling member (not shown) of the first plate is coupled with the coupling member (not shown) of the second plate 100 by bolts.

Further, it is described above that the first plate 100, the monocell 500, and the second plate 200 are sequentially positioned and fastened in the receiving groove 11 of the lower chamber 10 of the gas analysis device, but the present invention is not limited to this example. It is possible that the monocell 400 is received in the pressurizing jig of the present invention, and then the pressurizing jig, in which the fastening member 120 of the first plate is coupled with the coupling hole of the second plate 100, is mounted in the receiving groove 11.

In addition, by providing a separate pressurizing fastening hole (not shown) through which the fastening member 120 can pass in the upper chamber, the fastening member 120 may also press the monocell 500 by fastening the upper chamber, the first plate, and the second plate through the pressurizing fastening hole (not shown).

As described above, the gas analysis device of the monocell according to the preferred embodiment of the present invention may collect the internal gases of the monocell through the gas hole 21 and the collecting tube 22. In order to implement a safe and stable secondary battery by analyzing the collected internal gases as described above, the gas analysis device of the monocell according to a preferred embodiment of the present invention includes: an analysis module 40 for analyzing the internal gases introduced from the upper chamber 20; a charge/discharge module 50 for charging and discharging the monocell; a temperature measuring module 60 for measuring the temperature of the monocell; a display module 70 for outputting the analysis result of the internal gases of the monocell as an image; and a controller 80 for controlling the driving of the modules.

First, the analysis module 40 is a device for analyzing the internal gases collected by the collecting tube 22. As shown in FIG. 6, the analysis module 40 includes a gas tube 42, one end of which is connected to the other end of the collecting tube 22. Therefore, the analysis module 40 may receive the internal gases from the collecting tube 22, and may generate data on the composition, mass, volume, and the like of the internal gases by quantitatively and qualitatively analyzing the internal gases.

Next, the charge/discharge module 50 is a member for charging and discharging the monocell mounted on the receiving groove 11. The charge/discharge module includes a charge/discharge unit 52 for charging and discharging a monocell, a connecting member 54 electrically connecting the charge/discharge unit to the monocell, and a measuring unit 56 for measuring voltage and current which is applied to the monocell or which the monocell applies.

The charge/discharge unit 52 is connected to the electrode lead (not shown) of the monocell by the connecting member 54 to charge and discharge the monocell. The structure of the connecting member 54 is not specifically limited. For example, the connecting member 54 includes a pair of electrical wires electrically connecting the electrode leads of the monocell with the charge/discharge unit 52. A pair of electrical wires respectively extend to the inside of the receiving groove 11 through the charge/discharge holes 23 of the upper chamber 20, and terminals provided at the ends of the electrical wires are electrically connected to the electrode leads of the monocell, respectively.

The measuring unit 56 measures the voltage and current, which is applied to the monocell or which the monocell applies, and transmits the measured voltage and current to the controller 80. The controller 80 combines the voltage and current data received from the measuring unit 56 with the quantitative and qualitative analysis data of the internal gases received from the analysis module 40, to thereby generate data for specific voltages and specific currents at which internal gases are generated.

The temperature measuring module 60 is a member for measuring the temperature of the monocell mounted on the receiving groove 11. The temperature measuring module 60 includes a temperature sensing member for measuring the temperature of the monocell, a heating unit 64 for raising the temperature of the monocell, and a cooling unit 66 for lowering the temperature of the monocell.

The structure of the temperature sensing member is not particularly limited. For example, the temperature measuring module 50 extends into the receiving groove 11 through the temperature sensing hole formed in the upper chamber, and the bead is installed in contact with the monocell. Then, the temperature measuring module may measure the temperature of the monocell by measuring the voltage generated in the electrical circuit of the temperature measuring module connected with the conductive wires as the temperature of the bead changes.

The heating unit 64 is an essential member necessary to simulate a medium-large cell using a monocell. In general, the voltage and temperature profiles according to the monocell's state of charge (SOC) are different from those of medium-large cells. However, when the monocell is heated, the voltage and temperature profiles according to the state of charge become similar to those of the medium-large cells. Therefore, in the present invention using a monocell for the internal gas analysis of the medium-large cell, the heating unit 64 capable of heating the monocell is an essential member for simulating the medium-large cell.

The heating unit 64 may be installed to be in contact with at least one of the upper chamber and the lower chamber, and heat the monocell accommodated in the receiving groove 11 by applying heat to at least one of the upper chamber and the lower chamber.

The cooling unit 66 may be installed to be in contact with at least one of the upper chamber and the lower chamber, and may cool at least one of the upper chamber and the lower chamber to cool the monocell accommodated in the receiving groove 11.

The structure of the heating unit 64 and the cooling unit 66 is not particularly limited, and a heating device and a cooling device which are generally used may be used as the heating unit 64 and the cooling unit 66. The temperature change generated in the monocell by the heating unit 64 and the cooling unit 66 may be measured in real time by the temperature sensing member.

The temperature measuring module transmits the temperature of the secondary battery measured by the temperature sensing member to the controller 80. The controller 80 combines the temperature data received from the temperature measuring module 56 with the quantitative and qualitative analysis data of the internal gases received from the analysis module 40, to thereby generate data for specific temperatures at which internal gases are generated.

Next, the display module 70 is a device for displaying data collected by the modules included in the gas analysis device of the secondary battery cell according to the preferred embodiment of the present invention. For example, the display module 70 may display quantitative and qualitative analysis data of the internal gases, data on specific voltages or specific currents at which the internal gases are generated, and data on specific temperatures at which the internal gases are generated.

As such, when real-time analysis of the amount and composition of the gases generated during the initial charging of the monocell is performed, the pressurizing jig of the monocell for gas analysis according to the present embodiment can be used to facilitate the real-time analysis of the amount and composition of the generated gases.

While the present invention has been particularly shown and described with reference to exemplary embodiments thereof, it is to be understood that the invention is not limited to the disclosed embodiments, but, on the contrary, is intended to cover various modifications and equivalents included within the spirit and scope of the appended claims.

| [Description of Symbols] | |
|---|---|
| 100: first plate | 110: first groove |
| 120: fastening member | 200: second plate |
| 210: second groove | 220: fastening hole |
| 230: gas passage part | 300: first auxiliary pad |
| 400: second auxiliary pad | 500: monocell |
| 10: lower chamber | |
| 11: receiving groove | 13: sealing groove |
| 15: sealing member | 17: lower coupling hole |
| 20: upper chamber | |
| 21: gas hole | 22: collecting tube |
| 23: charge/discharge hole | 23a: sealing material |
| 25: upper coupling hole | |
| 30: coupling member | |
| 32: coupling bolt | 34: nut |
| 40: analysis module | |
| 50: charge/discharge module | |
| 52: charge/discharge unit | 54: measuring unit |
| 60: temperature measuring module | |
| 62: temperature sensing member | 64: heating unit |
| 66: cooling unit | |
| 70: display module | |
| 80: controller | |

The invention claimed is:

1. A gas analysis device of a monocell, comprising:
a lower chamber which has a shape corresponding to a pressurizing jig and includes a receiving groove into which the pressurizing jig is detachably fitted; and
an upper chamber including a gas hole which penetrates the upper chamber so as to be linked to the receiving groove and discharges internal gases generated in the monocell, a collecting tube connected to the gas hole which guides the internal gases discharged through the gas hole to an outside, and a charge/discharge hole through which a connecting member, which electrically connects a charge/discharge unit to the monocell, penetrates,
wherein the pressurizing jig comprises: a first plate and a second plate which face each other having the monocell therebetween; a first auxiliary pad between the first plate and the monocell; and a second auxiliary pad between the second plate and the monocell, and
each of the first plate and the second plate contains a thermosetting resin.

2. The gas analysis device of claim 1, further comprising:
an analysis module for the internal gases flown in from the upper or lower chamber;
a charge/discharge module charging or discharging the monocell mounted on the receiving groove;
a temperature measuring module measuring a temperature of the monocell;
a display module displaying an analysis result for the internal gases of the monocell; and a controller controlling operation of the analysis, charge/discharge, temperature measuring, and display modules.

3. The gas analysis device of claim 2, wherein the temperature measuring module comprises:
a temperature sensing member for measuring the temperature of the monocell;
a heating unit raising the temperature of the monocell; and
a cooling unit lowering the temperature of the monocell.

4. The gas analysis device of claim 1, wherein the charge/discharge hole is sealed with a sealing material that permits penetration of the connecting member through the charge/discharge hole.

5. The gas analysis device of claim 1, wherein the first plate has a quadrangular shape and includes at least one fastening member in at least one corner.

6. The gas analysis device of claim 1, wherein the second plate has a quadrangular shape and includes at least one fastening hole in at least one corner.

7. The gas analysis device of claim 1, wherein a location of the fastening member corresponds to a location of the fastening hole.

8. The gas analysis device of claim 1, wherein the second plate includes a gas passage part through which internal gases of the monocell are movable.

9. The gas analysis device of claim 1, wherein the first plate includes a first groove in which an electrode lead of the monocell is positioned.

10. The gas analysis device of claim 9, wherein the electrode lead is connected to a charge/discharge module charging or discharging the monocell.

11. The gas analysis device of claim 1, wherein the second plate includes a second groove in which an electrode lead of the monocell is positioned.

12. The gas analysis device of claim 1, wherein the thermosetting resin is Bakelite.

13. The gas analysis device of claim 1, wherein the first auxiliary pad and the second auxiliary pad comprise silicon rubber.

14. The gas analysis device of claim 1, wherein a thickness of each of the first plate and the second plate is between 1 and 20 mm.

15. The gas analysis device of claim 1, wherein a thickness of each of the first auxiliary pad and the second auxiliary pad is between 1 to 10 mm.

* * * * *